United States Patent [19]

Breglia De Belcoure et al.

[11] Patent Number: 5,510,534
[45] Date of Patent: Apr. 23, 1996

[54] PROCESS FOR REDUCING THE NITROSAMINE CONTENT OF HERBICIDES

[75] Inventors: Maria D. C. Breglia De Belcoure; Marta M. D. C. Ruiz, both of Buenos Aires, Argentina

[73] Assignee: Atanor S.A., Buenos Aires, Argentina

[21] Appl. No.: 408,875

[22] Filed: Mar. 23, 1995

[30] Foreign Application Priority Data

Jan. 4, 1995 [AR] Argentina ................................. 330645

[51] Int. Cl.$^6$ .......................... A01N 33/06; C07C 209/84
[52] U.S. Cl. .......................... 564/437; 504/347; 564/112; 564/441
[58] Field of Search .................... 564/112, 437, 564/441; 504/347

[56] References Cited

U.S. PATENT DOCUMENTS

| | | | |
|---|---|---|---|
| 4,127,610 | 11/1978 | Eizember | 260/582 |
| 4,134,917 | 1/1979 | Ross et al. | 260/577 |
| 4,185,035 | 1/1980 | Eizember et al. | 260/577 |
| 4,226,789 | 10/1980 | Eizember et al. | 260/397.7 |
| 4,675,445 | 6/1987 | Davis et al. | 564/437 |
| 4,876,388 | 10/1989 | Ravetta | 564/437 |
| 5,196,585 | 3/1993 | Wirth | 564/437 |
| 5,405,999 | 4/1995 | Donadello | 564/437 |

*Primary Examiner*—Richard L. Raymond
*Attorney, Agent, or Firm*—Banner & Allegretti, Ltd.

[57] ABSTRACT

The present invention is directed to a process for reducing the nitrosamine content in a herbicide derived from dinitroaniline. The herbicide is treated with an aqueous solution of alkaline or ammonium persulfate in a proportion of at least 0.5% w/w relative to the weight of the herbicide to form an aqueous suspension. The suspension is heated to at least 70° C., and the herbicide is separated from the suspension.

8 Claims, No Drawings

PROCESS FOR REDUCING THE NITROSAMINE CONTENT OF HERBICIDES

This invention relates to a process for reducing to a level of 0.5 mg/Kg (ppm=parts per million) or less the content of nitrosamines in herbicides, particularly of alkylnitrosamines, which are reaction products between a nitroso group and an alkylamine.

The presence of such compounds, mainly in herbicides, has been a matter of concern for scientists as well as manufacturers, since it has been shown that N-nitroso compounds—which include, among others, alkylnitrosamines—are carcinogenic for many mammals who are exposed to them through the ingestion of vegetables treated with said products.

Since numerous herbicides, for example substituted dinitroanilines, contain these compounds, the Environmental Protection Agency (EPA) has established very low tolerance limits for nitrosamine content. Specifically, in the case of Trifluralin, the maximum nitrosamine content allowed by the EPA is 0.5 ppm. For this reason, several attempts have been made to reduce or eliminate these compounds from herbicides, either by eliminating the nitrosamine precursors from the raw materials or by decreasing or eliminating nitrosamines from the finished product.

The herbicides derived from dinitroaniline can be represented by the following general formula (I)

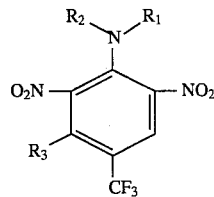

where $R_1$ and $R_2$ are alkyl($C_1$–$C_5$) groups; and $R_3$ is a hydrogen atom or an amino group.

In Trifluralin $R_1$=$R_2$=propyl and $R_3$=H

Among the nitrosamines that can be found in the dinitroaniline derivatives are N-nitroso-dipropylamine (NDPA), N-nitroso-ethylalylamine (EMANA), N-nitroso-ethylbutylamine (BENA), N-nitroso-diethylamine (NDEA), N-nitroso-dibutylamine (NDBA).

Those nitrosamines of the general formula

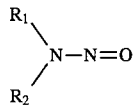

can be readily obtained through the action of nitrous acid, a nitrite in an acid medium, or other nitrosating agents, on the corresponding secondary amine.

According to N. T. Crosby (Residue Reviews Vol. 64 1976), who summarizes the content of numerous Chemistry books in relation to this matter, the chemical properties of nitrosamines vary according to the nature of the substituent groups ($R_1$ and $R_2$). Simple dialkylnitrosamines volatilize easily in a water vapor atmosphere. This property has been used to classify nitroso compounds into two groups: those compounds that volatilize easily and those with low volatility. In addition, nitrosamines show weak acid properties and can be eliminated in the form of salts of aqueous solutions by treatment with potassium carbonate. These nitroso compounds can be subjected to numerous reactions like hydrolysis, reduction, oxidation, cyclization and photochemical transformation. Further information on the chemical activity of these compounds can be found in several chemistry books like: SIDGWICK (1966), SMITH (1966), FEVER (1969) and CROSAY and SAWYER's review (1976).

Dialkylnitrosamines are stable in the presence of strong alkalis but the nitroso group is lost by heating with strong acids in an inverse reaction to synthesis. Hydrogen bromide in glacial acetic acid was analytically used as de-nitrosating agent (Eisenbrand and Preusman, 1970). They react to hydrochloric acid and the secondary amine regenerates.

Nitrosamines oxidize with strong oxidating agents like, for example, trifluoroperacetic acid (EMMONS, 1954) and nitric acid.

Nitrosamines are photosensitive and upon exposure to ultraviolet radiation they produce mainly secondary amines.

On the basis of these well known chemical and physicochemical properties of nitrosamines, many works describe different attempts to eliminate these compounds from herbicides derived from dinitroalanine. The following patents are examples of the numerous efforts aimed at reducing and/or eliminating nitrosamines from said herbicides:

U.S. Pat. No. 4,127,610

The nitrosamine content of herbicides derived from dinitrosaniline is reduced by treatment with molecular bromine ($Br_2$), molecular chlorine ($Cl_2$) and/or other chlorating and bromating agents like N-bromosuccinimide, N-chlorosuccinimide, bromine chloride, piridine perbromide and pirimidine bromine perbromide. However, as revealed in said patent, the use of 10% $Br_2$ produces side effects, such as polymerization and, in addition, under the given reaction conditions, more nitrosamines could be formed, which is a problem for the application of this method.

U.S. Pat. No. 4,134,917

Describes a de-nitrosating process for organic N-nitrosamines by the addition of an aldehyde or ketone in the presence of a strong acid. This process requires great quantities of hydrochloric acid, and consequently produces very large effluents containing it.

U.S. Pat. No. 4,185,035

The nitrosamine content of dinitroaniline derivates is reduced by treatment with inorganic halides, such as $PCl_3$, $PBr_3$, $TiCl_4$, $SO_2Cl_2$, but these halides are difficult to handle because they are corrosive and toxic and some of them produce toxic byproducts that add difficulties to the treatment of effluents. In any way, the concentration of nitrosamines after the treatment is still 3.8 ppm, which is high for EPA's requirements.

U.S. Pat. No. 4,226,789

The nitrosamine content is reduced by heating with concentrated hydrochloric acid or gaseous hydrochloric acid. Although the purpose of the process is achieved, it requires important amounts of 20–38% hydrochloric acid or gaseous hydrochloric, which upon neutralization, generate a substantial volume of unwanted effluents, of difficult final disposal.

U.S. Pat. No. 4,675,445

The nitrosamine content of herbicides derived from dinitroaniline is reduced by treatment with acid halides. This process generates acid effluents that require neutralization.

U.S. Pat. No. 4,876,388

Produces de elimination of nitrosamines contained in Trifluralin by bubbling through the melted compound a stream of saturated vapor at 105°–110° C. in an amount ranging from 1 to 4 times the weight of the Trifluralin under treatment. The process generates a great volume of effluents.

However, the problem of the nitrosamines contained by herbicides derived from dinitroaniline is not completely solved by simply trying to reduce and/or eliminate them from the herbicide, since a solution should also include preventing the generation of new nitrosamines during the formulation and/or storage of the technical product. Some of the methods for elimination, for example the method that uses hydrochloric acid, do not inhibit later formation of nitrosamines. For this reason it is necessary to add a treatment with sodium sulfite after the first treatment (U.S. Pat. No. 5,196,585) to eliminate some of the precursors of nitrosamines.

We have found that, surprisingly, the treatment of herbicides derived from dinitroaniline with oxidants like, for example, sodium, potassium or ammonium persulfates in an aqueous, basic or acid medium, not only decreases the nitrosamine content to values such as those required by the E.P.A., but also does not permit the generation of new nitrosamines upon long storage and/or prolonged heating. In addition, it should be pointed out that, although the herbicide is treated with an oxidant like persulfate, no degradation is produced.

EXAMPLES

1. Treatment with ammonium persulfate 1.1 To 400 g of melted humid raw Trifluralin with a nitrosamine content of 10 ppm, 6.4 g ammonium persulfate (1.6% w/w) and 40 g water were added, heating to 90° C. and stirring during 1 hour. The treated herbicide was separated, washed, and the melted herbicide was dried. The nitrosamine content was <0.2 ppm.

Reheating of the Trifluralin did not produce new nitrosamines. 1.2 To 400 g of melted humid raw Trifluralin with a nitrosamine content of 45 ppm, 6.4 g ammonium persulfate (1.6% w/w) and 40 g water were added. The mixture was heated to 90° C. and stirred during 1 hour. The treated Trifluralin was separated, and the above treatment with 1.6 w/w ammonium persulfate and 40 g water was repeated. The melted product was washed and dried. The nitrosamine content of Trifluralin was <0.2 ppm.

Reheating of this Trifluralin did not produce new nitrosamines.

2. Treatment with alkaline persulfate 2.1 To 500 g of melted humid raw Trifluralin with a nitrosamine content of 10 ppm, 8 g potassium persulfate (1.6% w/w) and 150 g water were added. The mixture was heated to 90° C. and stirred during 1 hour. The treated Trifluralin was separated, washed and the melted herbicide was dried. The nitrosamine content of Trifluralin was <0.2 ppm.

Reheating of this Trifluralin did not produce new nitrosamines. 2.2 To 500 g of melted humid raw Trifluralin with a nitrosamine content of 95 ppm, 8 g ammonium persulfate (1.6% w/w) and 150 g water were added. The mixture was heated to 90° C. and stirred during 1 hour. The treated Trifluralin was separated. It contained 20 ppm nitrosamine. The Trifluralin was washed and the above treatment with 8 g potassium persulfate (1.6 w/w) and 150 g water was repeated. The melted product was washed and dried. The nitrosamine content of Trifluralin was <0.5 ppm.

Reheating of this Trifluralin did not produce new nitrosamines.

We claim:

1. Process for reducing the nitrosamine content in a herbicide derived from dinitroaniline comprising:

treating the herbicide with an aqueous solution of alkaline or ammonium persulfate in a proportion of at least 0.5% w/w relative to the weight of the herbicide to form an aqueous suspension;

heating the suspension to at least 70° C.; and separating the herbicide from the suspension.

2. The process of claim 1 wherein the nitrosamine content is reduced to a level of 0.5 mg/kg or less.

3. The process of claim 1 further comprising treating the herbicide with an alkaline persulfate.

4. The process of claim 3 wherein the alkaline persulfate is sodium or potassium persulfate.

5. The process of claim 1 wherein the proportion of persulfate relative to the weight of the herbicide is 1.6% w/w.

6. The process of claim 1 wherein the suspension is heated to at least 90° C.

7. The process of claim 1 wherein the herbicide is derived from dinitroaniline in a wet and melted condition and contains at least 0.5 mg/kg nitrosamine.

8. The process of claim 1 wherein the aqueous suspension is heated for at least 30 minutes.

\* \* \* \* \*